(12) United States Patent
Beller et al.

(10) Patent No.: US 9,238,607 B1
(45) Date of Patent: Jan. 19, 2016

(54) PROCESS FOR THE CATALYTIC PRODUCTION OF UNSATURATED ALDEHYDES

(71) Applicant: Leibniz-Institut für Katalyse e.V. an der Universität Rostock (LIKAT), Rostock (DE)

(72) Inventors: Matthias Beller, Nienghagen (DE); Ralf Jackstell, Cuxhaven (DE); X. Fang, Shanghai (CN)

(73) Assignee: EVONIK INDUSTRIES AG, Marl (DE)

( * ) Notice: Subject to any disclaimer, the term of this patent is extended or adjusted under 35 U.S.C. 154(b) by 0 days.

(21) Appl. No.: 14/600,424

(22) Filed: Jan. 20, 2015

(30) Foreign Application Priority Data

Jan. 22, 2014 (DE) .......................... 10 2014 201 122

(51) Int. Cl.
*C07C 45/50* (2006.01)
(52) U.S. Cl.
CPC .................................... *C07C 45/505* (2013.01)
(58) Field of Classification Search
CPC ....................................................... C07C 45/50
USPC ................................................. 568/454, 455
See application file for complete search history.

(56) References Cited

U.S. PATENT DOCUMENTS

| 4,567,306 A * | 1/1986 | Dennis et al. ................. 568/455 |
| 4,687,866 A | 8/1987 | Oswald et al. |
| 4,982,007 A * | 1/1991 | Shimizu et al. ............... 568/429 |
| 8,927,776 B2 * | 1/2015 | Franke et al. ................. 568/444 |
| 2009/0227801 A1 | 9/2009 | Ahlers et al. |

FOREIGN PATENT DOCUMENTS

| DE | 102004052040 A1 | 4/2006 |
| KR | 20070017908 A | 2/2007 |
| WO | 8001691 A1 | 8/1980 |

OTHER PUBLICATIONS

German Search Report for corresponding application DE 10 2014 201 122.1 dated Oct. 2, 2014.
European Search Report for corresponding application EP 15152138.2 dated Jun. 19, 2015.

\* cited by examiner

*Primary Examiner* — Sikarl Witherspoon
(74) *Attorney, Agent, or Firm* — Smith, Gambrell & Russell, LLP

(57) ABSTRACT

The invention concerns a process for the catalytic production of unsaturated aldehydes by reacting an olefin in the presence of carbon monoxide and hydrogen, a rhodium compound and organic phosphorus-containing ligands in an organic solvent as well as a co-catalyst formed from a weak organic acid and an organic amine.

13 Claims, No Drawings

PROCESS FOR THE CATALYTIC PRODUCTION OF UNSATURATED ALDEHYDES

The invention concerns a process for the catalytic production of unsaturated aldehydes by reaction of an alkene (olefin) in the presence of synthesis gas (carbon monoxide and hydrogen), a rhodium compound and organic phosphorus-containing ligands in an organic solvent as well as a co-catalyst formed from a weak organic acid and an organic amine.

α,β-unsaturated aldehydes constitute an important class of fine chemicals which have a broad spectrum of application in the food industry and the cosmetics and pharmaceuticals industries. Because of their diverse fields of application, they are thus sought-after intermediate and end products in the fine chemicals and industrial chemistry industries. Because of their immense importance, many production methods have been proposed for them. These include the oxidation of allyl alcohols, Peterson olefination, formylation, Heck reactions, aldol condensations, Saegusa oxidations and hydroformylation of alkynes. Each of those protocols has its own special features. Some of them suffer from major disadvantages such as poor yields, harsh reaction conditions, high catalyst loads as well as the generation of environmentally damaging halogenated waste products, limited chemo-, regio- and stereoselectivity and expensive product isolation methods. Frequently also, the starting materials are difficult to access. The hydroformylation of olefins to aldehydes has been known for many years. Because the aldehyde group is chemically versatile and can be reacted further by reduction, oxidation or other reactions to form alcohols, amines, acid derivatives, aldol condensation products and many other products, aldehydes are of major importance. Hydroformylation can also be integrated into tandem or domino reactions. Reduction, nucleophilic addition or aldol condensation can be carried out directly under the reaction conditions for hydroformylation ((a) Eilbracht, P.; Bärfacker, L.; Buss, C.; Hollmann, C.; Kitsos-Rzychon, B. E.; Kranemann, C. L.; Rische, T.; Roggenbuck, R.; Schmidt, A. *Chem. Rev.* 1999, 99, 3329; (b) Eilbracht, P.; Schmidt, A. M. *Top. Organomet. Chem.* 2006, 18, 65-95). Additional reagents, products or variations to the reaction conditions optimized for hydroformylation can suppress or inhibit the initial hydroformylation step which is not trivial. Aldol products are usually observed as by-products in olefin reactions under hydroformylation conditions. Either an aldol addition of the enolized oxoaldehyde molecule to an oxoaldehyde can occur as a homo-aldol addition, or one of the two reagents which are present under the hydroformylation conditions can undergo a cross-aldol addition with the usual selectivity problems.

The hydroformylation/aldol reaction usually results in a low chemoselectivity and/or a low yield of the desired unsaturated aldehydes, in particular because the corresponding saturated aldehydes and alcohols are strongly suppressed under harsh conditions: see, for example, Knifton, J. F.; Lin, J. J. *J. Mol. Catal.* 1993, 81, 1. On the other hand, over the last two decades, Eilbracht et al. have reported intramolecular hydroformylation/aldol reactions in the synthesis of carbocyclic ring products, wherein unsaturated silylenol ether was used as the substrate in order to avoid chemo- and regioselectivity problems: see, for example, Hollmann, C.; Eilbracht, P. *Tetrahedron* 2000, 56, 1685. Furthermore, that group used the strategy of combining metallocatalysis and organocatalysis in order to carry out intermolecular hydroformylation/aldol reactions, wherein cyclic olefins or styrenes were used as the substrate in order to avoid regioselectivity problems in the hydroformylation reactions, and acetone was used as the C-nucleophile: see, for example, Chercheja, S.; Rothenbücher, T.; Elibracht. P. *Adv. Synth. Catal.* 2009, 351, 339.

However, no selective and efficient intermolecular hydroformylation/aldol reactions of olefins to form α,β-unsaturated aldehydes could be carried out; until now, this has constituted a difficult problem.

Thus, the aim of the invention is to synthesize unsaturated aldehydes by a simple reaction from easily accessible starting compounds.

It has been discovered that unsaturated α,β-aldehydes are obtained in one process step with high selectivities, conversions and service lives if an alkene (olefin) is reacted in the presence of a synthesis gas formed from carbon monoxide and hydrogen and a rhodium catalyst in combination with an organic phosphorus ligand in an organic solvent as well as with a co-catalyst formed by an organic amine and a weak organic acid. The reaction proceeds via hydroformylation of the olefin to form the aldehyde, followed by aldol condensation to form the target compounds.

The olefins which are used as the starting materials in accordance with the invention may be terminal alkenes, cycloalkenes and aromatic and heteroaromatic olefins containing 2 to 40 carbon atoms, or mixtures thereof, which may or may not be branched and/or substituted. The terms "alkene" and "olefin" are terms which are synonymous.

These substituents may be selected from groups comprising alkyl groups preferably containing 1 to 12 C atoms, cycloalkyl groups preferably containing 4 to 10 C atoms, alkenyl groups preferably containing 1 to 12 C atoms, hydroxyl groups, ether groups, ester groups, carboxyl groups, nitro groups, amino groups, halogens (Cl, F, Br, I), aryl or aralkyl groups as well as heteroaromatic hydrocarbons and alkyl residues, preferably containing 1 to 6 C atoms, which may in turn be substituted with the said substituents. The term "aryl" means phenyl, naphthyl, anthryl, for example. "Heteroaromatic compounds" are heteroaryl residues with a ring structure containing one or more heteroatoms (O, N, S).

The organic solvent is preferably selected from the group comprising acetic acid (methyl, ethyl or n-butyl) esters and N-methylpyrrolidone. Acetic acid ethyl ester is particularly preferred.

The rhodium catalyst acts as a hydroformylation catalyst. Preferably, a rhodium complex is used which contains at least one of the following compounds: CO and/or olefin, for example cyclooctadienyl, norbornadienyl, ethenyl, cyclopentadienyl, halide, for example $Cr^-$, $Br^-$, tetrafluoroborate, hydride ($H^-$), carboxylate, for example acetate, acetylacetonate, nonanoate and/or sulphate. Examples of particularly preferred rhodium complexes which may be used are $Rh(CO)_2(acac)$, Rh(II)acetate (dimer), $RhCODBF_4$, $RhNBD BF_4$, Rh (II)octanoate (dimer) and hexarhodium-hexadecacarbonyl. The use of $Rh(CO)_2(acac)$ is particularly preferred.

Any phosphorus-containing ligand which can form a dative bond with the rhodium centre can be used as the phosphorus-containing ligand. The ligands in this case may be both monodentate and also multidentate. Preferably, monodentate or bidentate phosphorus-containing ligands are used, for example monodentate phosphines, phosphites, phosphonites, phosphinites or bidentate phosphines, phosphonites, phosphites, phosphinites or mixed bidentate ligands such as phosphine/phosphite combinations, wherein the phosphorus is bonded to aryl and/or (cyclo)alkyl, aryloxy and/or (cyclo)alkoxy groups.

Particularly preferred ligands are selected from groups L1 to L7:

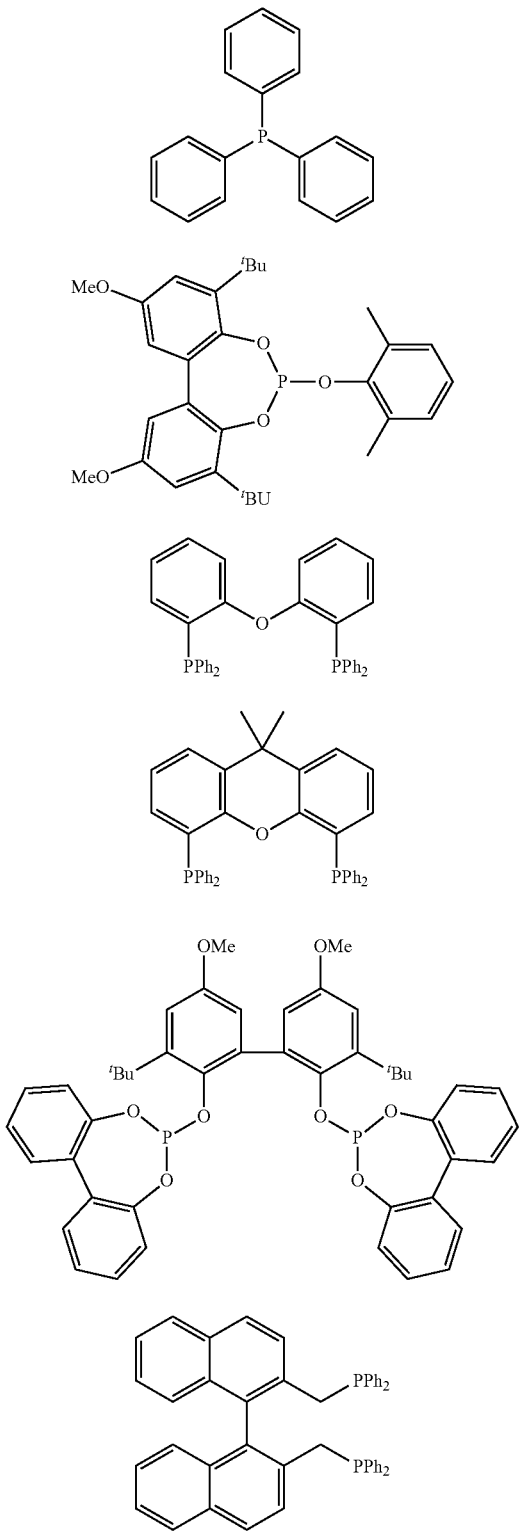

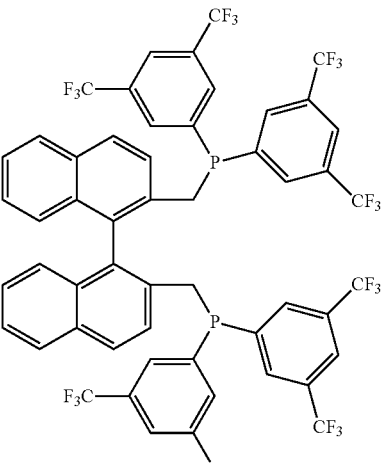

NAPHOS (L6=2,2'-bis(diphenylphosphino)methyl-1,1'-binaphthyl) is of particularly effective application in the process of the invention as a bidentate diphosphino ligand.

The rhodium:ligand ratio when using monodentate ligands is preferably 1:50, preferentially 1:10, and when using bidentate ligands, it is 1:10, preferably 1:2.

The co-catalyst used is a combination of an organic amine and a weak organic acid, preferably in a molar ratio of 2:1 to 1:2, particularly preferably in a ratio of 1:1.

Preferably, primary or secondary alkenes are used as the organic alkenes. Particularly preferably, the alkenes are selected from the group comprising pyrrolidine, piperidine, $C_1$-$C_{10}$ alkyl (or $C_5$-$C_{10}$ cycloalkyl)- or $C_1$-$C_{10}$-dialkyl (or $C_5$-$C_{10}$-cycloalkyl)amine and morpholine as well as piperazine, wherein the compounds may be substituted. Pyrrolidine is particularly preferred.

The weak organic acid is preferably selected from the group comprising $C_6$-$C_{15}$ aromatic carboxylic acids, aliphatic $C_1$-$C_{20}$ carboxylic acids and heteroaromatic carboxylic acids, wherein the compounds may be substituted. Examples of aromatic (hydrocarbon) residues are aryl residues, for example phenyl, naphthyl, anthryl.

The heteroaromatic compounds are aromatic compounds the ring structure of which contains one or more heteroatoms (O, N, S).

Examples of aromatic carboxylic acids are benzoic acids and naphthoic acids. Examples of aliphatic carboxylic acids which may be mentioned are acetic acid, nonanoic acid (pelargonic acid), and adipinic acid. Examples of heteroaromatic carboxylic acids are thiophene carboxylic acid, nicotinic acid and furan-2-carboxylic acid. Benzoic acid, acetic acid, nonanoic acid and thiophenic acid are particularly preferred.

The substituents may be the other ($C_1$ to $C_{12}$) alkyl or ($C_4$ to $C_8$) cycloalkyl groups, ($C_1$ to $C_{12}$) alkenyl groups, ether groups, ester groups, hydroxyl groups, carboxyl groups, nitro groups, amino groups, halogens (F, Cl, Br, I), aromatic hydrocarbons (aryl and aralkyl groups) and heteroaromatic hydrocarbons which have already been mentioned.

Particularly preferably, the following combinations are used in the process of the invention as the co-catalyst: pyrrolidine/benzoic acid, pyrrolidine/4-methoxy benzoic acid, pyrrolidine/4-(trifluoromethyl)benzoic acid, pyrrolidine/acetic acid, pyrrolidine/nonanoic acid or pyrrolidine/3-thiophene carboxylic acid. The pyrrolidine/benzoic acid combination is most particularly preferred.

Surprisingly, neither the use of a strong base such as NaOH nor an organic alkene alone, nor the use of a weak organic acid alone, results in the desired target compounds. In addition, the absence of a phosphorus ligand also means that the reaction of the invention to form the desired unsaturated aldehydes does not occur.

Only the combination of all of the components results in the highly selective synthesis of unsaturated aldehydes by reaction of an olefin in the presence of carbon monoxide and hydrogen.

In the process of the invention, the molar ratio of carbon monoxide to hydrogen is advantageously in the range 10:1 to 1:10, preferably 1:2. A ratio of 1:1 is the most suitable since in this case, no excess carbon monoxide or excess hydrogen has to be flushed out of the vessel in which the reaction is taking place.

Preferably, the reaction temperature at which the reaction is carried out is in the range 20° C. to 150° C., preferably 50° C. to 110° C.

Preferably, the pressure at which the process is carried out is in the range 1 to 50 bar, preferably in the range 3 to 12 bar.

The process is efficient and selective and is carried out under mild conditions. It results in good yields of the corresponding unsaturated aldehydes and effectively suppresses unwanted homo-aldol side reactions.

Surprisingly, moreover, it has been discovered that using the present process, cross aldol condensates can also be produced when an olefin is reacted with an appropriate aromatic or heteroaromatic aldehyde under the same conditions as the reaction described above. The process of the invention is thus also used for the production of cross aldol condensates. Any terminal alkenes, cycloalkenes or aromatic olefins, preferably containing 2 to 40 carbon atoms or mixtures thereof, which may or may not be substituted, are reacted with any aromatic or heteroaromatic aldehyde the aryl or heteroaryl residue of which also may or may not be substituted, in the presence of carbon monoxide and hydrogen as well as one of the rhodium catalysts cited above in combination with one of the organic phosphorus ligands cited above and one of the co-catalysts cited above formed by an organic amine and a weak organic acid in a polar solvent such as NMP (N-methyl pyrrolidine) or DMF (dimethylformamide) or without a solvent. The substituents may be any of those cited above. Particularly preferably, the reaction is carried out in NMP. The corresponding cross aldol condensates are obtained in good yields. The examples below serve to illustrate the process of the invention. The examples clearly show the very good yields and selectivities for the process of the invention.

EXAMPLES

Example 1

Reaction of 1-octene (1a) using Rh(CO)$_2$(acac) and various ligands L1-L7 as well as the co-catalysts listed in Table 1 to form the target product 3a in accordance with the following reaction equation:

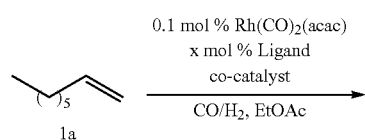

-continued

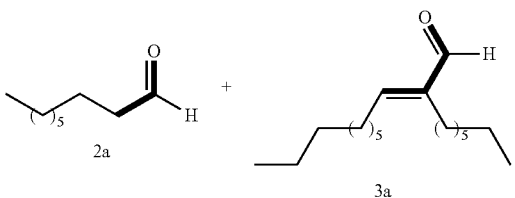

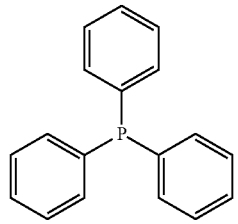
L1

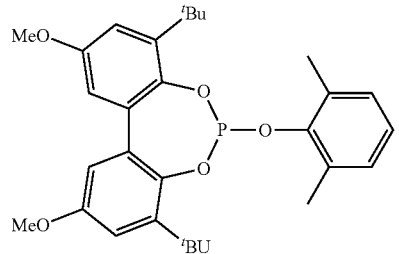
L2

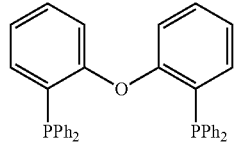
L3

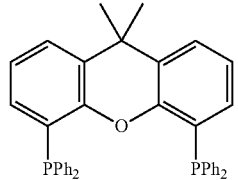
L4

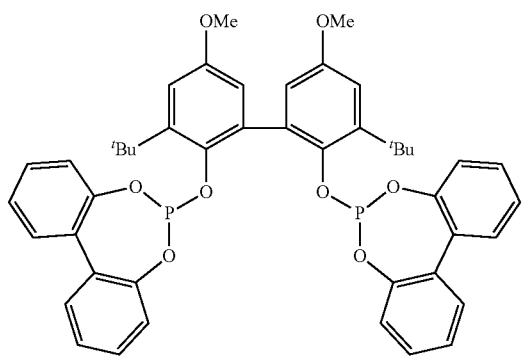
L5

-continued

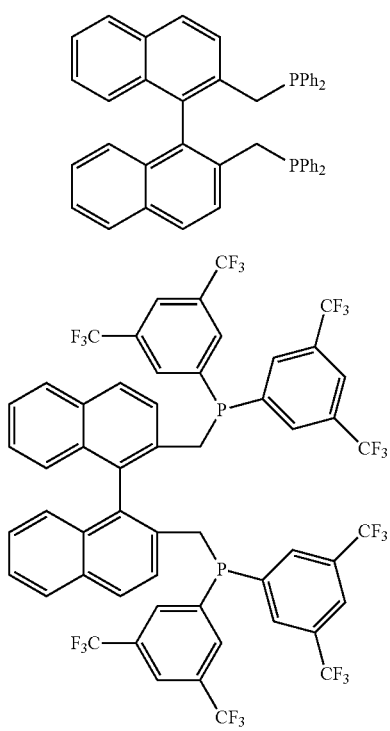

L6

L7

Table 1 lists the co-catalysts, ligands, conversions and yields.

Example 1.1

Table 1

A 25 mL Schlenk flask was filled with [Rh(CO)$_2$(acac)] (3.1 mg, 0.1 mol %), L6 (15.6 mg, 0.2 mol %) and EtOAc (16 mL) under argon. A vial (4 mL) was filled with NaOH (6 mg, 10 mol %) and a magnetic stirrer was placed in it. Next, 2 mL of the yellow solution from the Schlenk flask and 1a (235 μL, 1.5 mmol) was transferred to the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 1.2

Table 1

Analogous to Example 1.1, but L-proline (17.3 mg, 10 mol %) was used in place of NaOH.

TABLE 1

| Example[a] | Co-catalyst | Ligand | Conversion | 2a yield (n/iso) | 3a yield (E/Z) |
|---|---|---|---|---|---|
| 1.1 | NaOH (10 mol %) | L6 | 99% | 96% (76/24) | 0% |
| 1.2 | L-proline (10 mol %) | L6 | 87% | 76% (93/7) | 3% (89/11) |
| 1.3 | Pyrrolidine (10 mol %) | L6 | 97% | 79% (98/2) | 4% (99/1) |
| 1.4 | Benzoic acid (10 mol %) | L6 | 98% | 95% (95/5) | 0% |
| 1.5 | Pyrrolidine (10 mol %) and benzoic acid (10 mol %) | L6 | 100% | 3% (66/34) | 90% (96/4) |
| 1.6 | Pyrrolidine (10 mol %) and benzoic acid (10 mol %) | — | 12% | 0% | 0% |
| 1.7 | Pyrrolidine (10 mol %) and benzoic acid (10 mol %) | L3 | 36% | 10% (62/38) | 17% (>99/1) |
| 1.8 | Pyrrolidine (10 mol %) and benzoic acid (10 mol %) | L4 | 86% | 17% (50/50) | 39% (94/6) |
| 1.9 | Pyrrolidine (10 mol %) and benzoic acid (10 mol %) | L5 | 99% | 4% (1/99) | 58% (96/4) |
| 1.10 | Pyrrolidine (10 mol %) and benzoic acid (10 mol %) | L7 | 99% | 0% | 80% (96/4) |
| 1.11 | Pyrrolidine (5 mol %) and benzoic acid (5 mol %) | L6 | 98% | 3% (66/34) | 90% (96/4) |
| 1.12 | Pyrrolidine (2.5 mol %) and benzoic acid (2.5 mol %) | L6 | 100% | 14% (88/12) | 70% (95/5) |
| 1.13 | Pyrrolidine (5 mol %) and benzoic acid (5 mol %) | L6 | 98% | 0% | 68% (96/4) |

[a]65° C., 24 h, 10 bar synthesis gas (CO:H$_2$ = 1:1)

Example 1.3

Table 1

Analogous to Example 1.1, but pyrrolidine (12.3 μL, 10 mol %) was used in place of NaOH.

Example 1.4

Table 1

Analogous to Example 1.1, but benzoic acid (18.3 mg, 10 mol %) was used in place of NaOH.

Example 1.5

Table 1

Analogous to Example 1.1, but pyrrolidine (12.3 μL, 10 mol %) and benzoic acid (18.3 mg, 10 mol %) were used in place of NaOH.

Example 1.6

Table 1

A 25 mL Schlenk flask was filled with [Rh(CO)$_2$(acac)] (3.1 mg, 0.1 mol %), pyrrolidine (100 μL, 10 mol %), benzoic acid (146.4 mg, 10 mol %) and EtOAc (16 mL) under argon. Next, 2 mL of the yellow solution from the Schlenk flask and 1a (235 μL, 1.5 mmol) was transferred into a 4 mL vial using a syringe and a magnetic stirrer was placed in it. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 1.7

Table 1

A 25 mL Schlenk flask was filled with [Rh(CO)$_2$(acac)] (3.1 mg, 0.1 mol %), pyrrolidine (100 μL, 10 mol %), benzoic acid (146.4 mg, 10 mol %) and EtOAc (16 mL) under argon. A vial (4 mL) was filled with L3 (1.62 mg, 0.2 mol %) and a magnetic stirrer was placed in it. Next, 2 mL of the yellow solution from the Schlenk flask and 1a (235 μL, 1.5 mmol) was transferred into the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 1.8

Table 1

Analogous to Example 1.7, but L4 (1.74 mg, 0.2 mol %) was used in place of L3.

Example 1.9

Table 1

Analogous to Example 1.7, but L5 (2.36 mg, 0.2 mol %) was used in place of L3.

Example 1.10

Table 1

Analogous to Example 1.7, but L7 (3.58 mg, 0.2 mol %) was used in place of L3.

Example 1.11

Table 1

A 25 mL Schlenk flask was filled with [Rh(CO)$_2$(acac)] (3.1 mg, 0.1 mol %), pyrrolidine (50 μL, 5 mol %), benzoic acid (73.2 mg, 5 mol %) and EtOAc (16 mL) under argon. A vial (4 mL) was filled with L6 (1.95 mg, 0.2 mol %) and a magnetic stirrer was placed in it. Next, 2 mL of the yellow solution from the Schlenk flask and 1a (235 μL, 1.5 mmol) was transferred into the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 1.12

Table 1

Analogous to Example 1.11, but pyrrolidine (25 μL, 2.5 mol %) and benzoic acid (36.6 mg, 2.5 mol %) were used.

Example 1.13

Table 1

Analogous to Example 1.11, but after flushing the autoclave three times with nitrogen, it was pressurized to 5 bar with synthesis gas (CO: H$_2$=1:1).

Example 2

Reaction of 1-octene using Rh(CO)$_2$(acac) and L6 in accordance with the following equation and using the co-catalysts listed in Table 2:

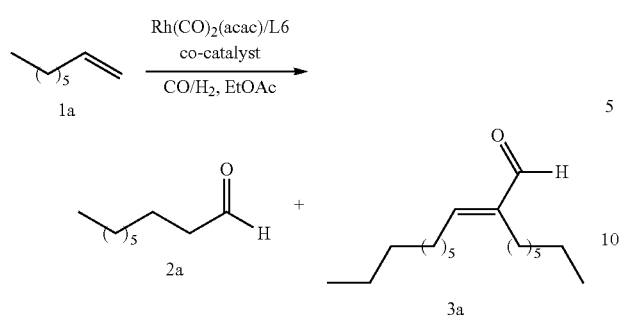

TABLE 2

| Example | Co-catalyst | Conversion | 2a yield (n/iso) | 3a yield (E/Z) |
|---|---|---|---|---|
| 2.1 | Pyrrolidine and benzoic acid | 98% | 3% (66/34) | 90% (96/4) |
| 2.2 | Piperidine and benzoic acid | 98% | 27% (63/37) | 62% (96/4) |
| 2.3 | Diethylamine and benzoic acid | 98% | 27% (93/7) | 68% (94/6) |
| 2.4 | n-Butylamine and benzoic acid | 89% | 26% (65/35) | 40% (95/5) |
| 2.5 | Pyrrolidine and AcOH | 97% | 14% (88/12) | 81% (97/3) |
| 2.6 | Pyrrolidine and nonanoic acid | 100% | 3% (65/35) | 90% (97/3) |
| 2.7 | Pyrrolidine and 4-methoxybenzoic acid | 98% | 6% (79/21) | 89% (97/3) |
| 2.8 | Pyrrolidine and 4-(trifluoromethyl)benzoic acid | 97% | 5% (79/21) | 89% (98/2) |
| 2.9 | Pyrrolidine and 3-thiophene carboxylic acid | 87% | 6% (75/25) | 79% (98/2) |

Example 2.1

Table 2

A 25 mL Schlenk flask was filled with [Rh(CO)$_2$(acac)] (3.1 mg, 0.1 mol %), L6 (15.6 mg, 0.2 mol %) and EtOAc (16 mL) under argon. A vial (10 mL) was filled with benzoic acid (18.3 mg, 5 mol %) and a magnetic stirrer was placed in it. Next, 4 ml of the yellow solution from the Schlenk flask and 1a (471 µL, 3 mmol) and pyrrolidine (12.3 µL, 5 mol %) were transferred into the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 2.2

Table 2

A 25 mL Schlenk flask was filled with [Rh(CO)$_2$(acac)] (3.1 mg, 0.1 mol %), L6 (15.6 mg, 0.2 mol %) and EtOAc (16 mL) under argon. A vial (10 mL) was filled with benzoic acid (18.3 mg, 5 mol %) and a magnetic stirrer was placed in it. Next, 4 ml of the yellow solution from the Schlenk flask and 1a (471 µL, 3 mmol) and piperidine (14.9 µL, 0.5 mol %) were transferred into the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 2.3

Table 2

Analogous to Example 2.2, but diethylamine (15.7 µL, 5 mol %) was added with a syringe in place of the piperidine.

Example 2.4

Table 2

Analogous to Example 2.2, but n-butylamine (14.8 µL, 5 mol %) was added with a syringe in place of the piperidine.

Example 2.5

Table 2

A 25 mL Schlenk flask was filled with [Rh(CO)$_2$(acac)] (3.1 mg, 0.1 mol %), L6 (15.6 mg, 0.2 mol %) and EtOAc (16 mL) under argon. A vial (10 mL) was filled with pyrrolidine (100 µL, 5 mol %) and a magnetic stirrer was placed in it. Next, 4 ml of the yellow solution from the Schlenk flask and 1a (471 µL, 3 mmol) and acetic acid (8.6 µL, 5 mol %) were transferred into the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 2.6

Table 2

A 25 mL Schlenk flask was filled with [Rh(CO)$_2$(acac)] (3.1 mg, 0.1 mol %), L6 (15.6 mg, 0.2 mol %) and EtOAc (16 mL) under argon. A vial (10 mL) was filled with pyrrolidine (100 µL, 5 mol %) and a magnetic stirrer was placed in it. Next, 4 ml of the yellow solution from the Schlenk flask and 1a (471 μL, 3 mmol) and nonanoic acid (26.4 μL, 5 mol %) were transferred into the vial using a syringe. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: $H_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 2.7

Table 2

Analogous to Example 2.6, but 4-methoxybenzoic acid (22.8 mg, 5 mol %) was added with a syringe in place of the nonanoic acid.

Example 2.8

Table 2

Analogous to Example 2.6, but 4-(trifluoromethyl)benzoic acid (28.5 mg, 5 mol %) was added with a syringe in place of the nonanoic acid.

Example 2.9

Table 2

Analogous to Example 2.6, but 3-thiophene carboxylic acid (19.2 mg, 5 mol ° A)) was added with a syringe in place of the nonanoic acid.

Example 3

Reaction of various olefins in accordance with the following reaction:

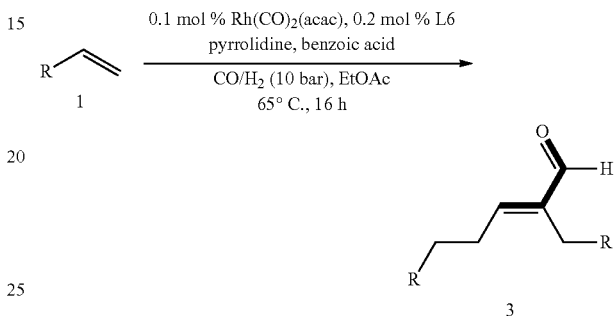

Table 3 shows the starting olefins, products and yields:

TABLE 3

| Example | 1 | 3 | Yield (E/Z) |
|---|---|---|---|
| 3.1 | 1a (1-octene) | 3 (branched α,β-unsaturated aldehyde) | 89% (96/4) |
| 3.2 | 1b (ethylene) | 3b | 98% (>99/1) |
| 3.3 | 1c (propene) | 3c | 69% (95/5) |
| 3.4 | 1d (1-butene) | 3d | 81% (97/3) |

TABLE 3-continued
| Example | 1 | 3 | Yield (E/Z) |
|---|---|---|---|
| 3.5 | 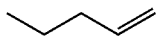<br>1e | 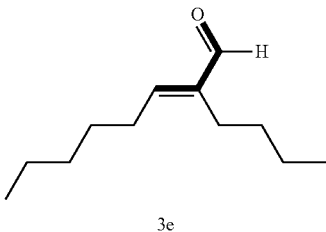<br>3e | 85% (>99/1) |
| 3.6 | 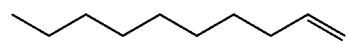<br>1f | 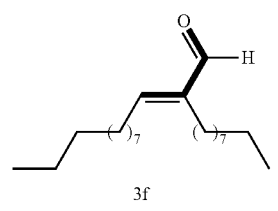<br>3f | 91% (97/3) |
| 3.7 | <br>1g | 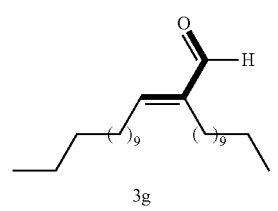<br>3g | 89% (97/3) |
| 3.8 | 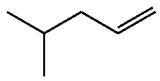<br>1h | 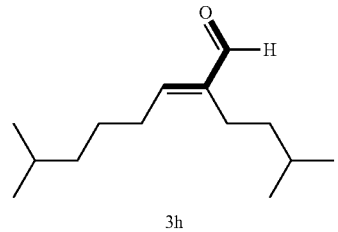<br>3h | 86% (99/1) |
| 3.9 | 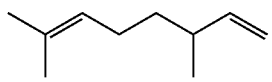<br>1i | 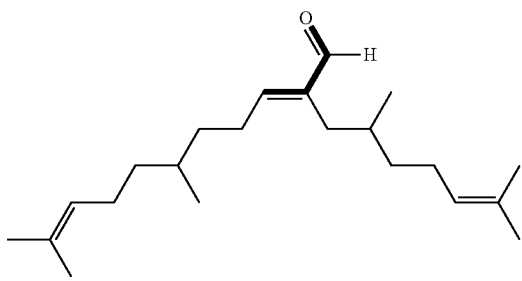<br>3i | 75% (97/3) |
| 3.10 | 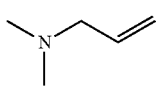<br>1j | 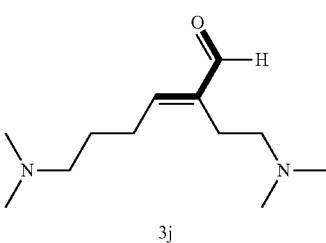<br>3j | 78% (>99/1) |

TABLE 3-continued

| Example | 1 | 3 | Yield (E/Z) |
|---|---|---|---|
| 3.11 | 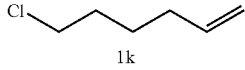 1k | 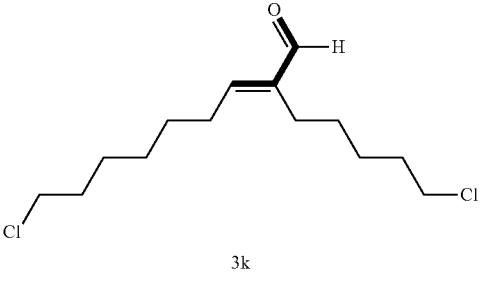 3k | 69% (97/3) |
| 3.12 | 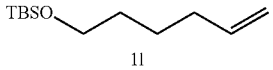 1l | 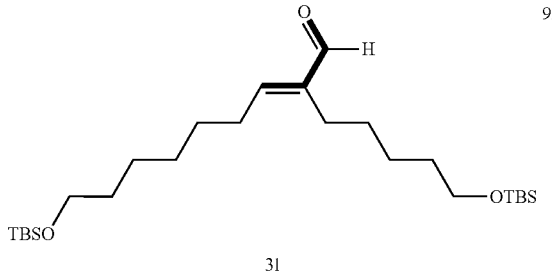 3l | 92% (95/5) |

TBS = tert-butyldimethylsilyl

Example 3.1

Table 3

A 100 mL steel autoclave was filled with [Rh(CO)$_2$(acac)] (3.87 mg, 0.1 mol %), L6 (19.52 mg, 0.2 mol %) and benzoic acid (91.5 mg, 5 mol %) under argon. Next, EtOAc (20 mL), pyrrolidine (62.54, 5 mol %) and 1a (2.35 mL, 15 mmol) was added under argon. The autoclave was pressurized to 10 bar with synthesis gas (CO: H$_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3a. The yield is the isolated yield.

Example 3.2

Table 3

Analogous to Example 3.1, but 1 b (420.8 mg, 15 mmol) was added under argon in place of the 1a. The autoclave was pressurized to 10 bar with synthesis gas (CO: H$_2$=1:1) and stirred for 16 hours at 65° C. After the reaction, the autoclave was cooled down using ice water and the pressure was released. The yield and selectivity were determined using GC/MS analysis.

Example 3.3

Table 3

Analogous to Example 3.1, but 1c (631.2 mg, 15 mmol) was added under argon in place of the 1a. The autoclave was pressurized to 10 bar with synthesis gas (CO: H$_2$=1:1) and stirred for 16 hours at 65° C. After the reaction, the autoclave was cooled down using ice water and the pressure was released. The yield and selectivity were determined using GC/MS analysis.

Example 3.4

Table 3

Analogous to Example 3.1, but 1d (841.7 mg, 15 mmol) was added under argon in place of the 1a. The autoclave was pressurized to 10 bar with synthesis gas (CO: H$_2$=1:1) and stirred for 16 hours at 65° C. After the reaction, the autoclave was cooled down using ice water and the pressure was released. The yield and selectivity were determined using GC/MS analysis. The reaction mixture was reduced under vacuum and purified by column chromatography over silica gel (eluent:ethyl acetate:heptane=1:30) to produce the product 3d. The yield is the isolated yield.

Example 3.5

Table 3

Analogous to Example 3.1, but 1e (1.64 mL, 15 mmol) was added under argon in place of the 1a. The autoclave was pressurized to 10 bar with synthesis gas (CO: H$_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3e. The yield is the isolated yield.

Example 3.6

Table 3

Analogous to Example 3.1, but 1f (2.84 mL, 15 mmol) was added under argon in place of the 1a. The autoclave was pressurized, to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3f. The yield is the isolated yield.

Example 3.7

Table 3

Analogous to Example 3.1, but 1g (3.33 mL, 15 mmol) was added under argon in place of the 1a. The autoclave was pressurized to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3g. The yield is the isolated yield.

Example 3.8

Table 3

Analogous to Example 3.1, but 1h (1.9 mL, 15 mmol) was added under argon in place of the 1a. The autoclave was pressurized to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3h. The yield is the isolated yield.

Example 3.9

Table 3

Analogous to Example 3.1, but 1i (2.73 mL, 15 mmol) was added under argon in place of the 1a. The autoclave was pressurized to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3i. The yield is the isolated yield.

Example 3.10

Table 3

Analogous to Example 3.1, but 1j (1.78 mL, 15 mmol) was added under argon in place of the 1a. The autoclave was pressurized to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3j. The yield is the isolated yield.

Example 3.11

Table 3

Analogous to Example 3.1, but 1k (1.99 mL, 15 mmol) was added under argon in place of the 1a. The autoclave was pressurized to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3k. The yield is the isolated yield.

Example 3.12

Table 3

Analogous to Example 3.1, but 1l (3.22 g, 15 mmol) was added under argon in place of the 1a. The autoclave was pressurized to 10 bar with synthesis gas (CO: $H_2$=1:1) and stirred for 16 hours at 65° C. After the reaction, the autoclave was cooled down using ice water and the pressure was released. The selectivity was determined using GC/MS analysis. The reaction mixture was reduced under vacuum and purified by column chromatography over silica gel (eluent:ethyl acetate:heptane=1:30) to produce the product 3l. The yield is the isolated yield.

Example 4

Reaction of compounds 1a and 4a for the production of cross aldol condensates in accordance with the following reaction, using NMP as the solvent.

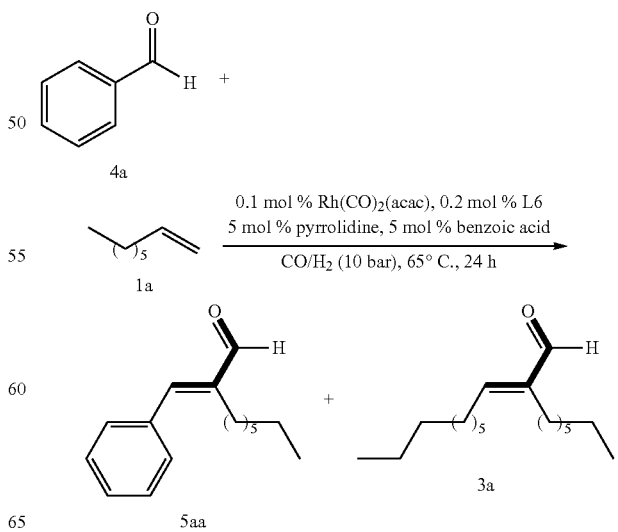

TABLE 4

| Example | Solvent | Conversion | 5aa yield (E/Z) | 3a yield (E/Z) |
|---------|---------|------------|-----------------|----------------|
| 4.1     | NMP     | 94%        | 90% (96/4)      | Trace          |

NMP = N-methyl-2-pyrrolidone

Example 4.1

Table 4

A vial (4 mL) was filled with [Rh(CO)$_2$(acac)] (0.387 mg, 0.1 mol %), L6 (1.95 mg, 0.2 mol %) and benzoic acid (9.15 mg, 5 mol %), NMP (2 mL), 1a (235 µL, 1.5 mmol) and 4a (153 µL, 1.5 mmol) and a magnetic stirrer was placed in it. This vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. After the reaction was ended, the autoclave was cooled to ambient temperature and the pressure was slowly released. Isooctane was added as the internal standard and the yield, conversion and the selectivity were determined using GC analysis.

Example 5

Production of cross aldol condensates from alkenes 1 and aldehydes 4 in accordance with scheme 1:

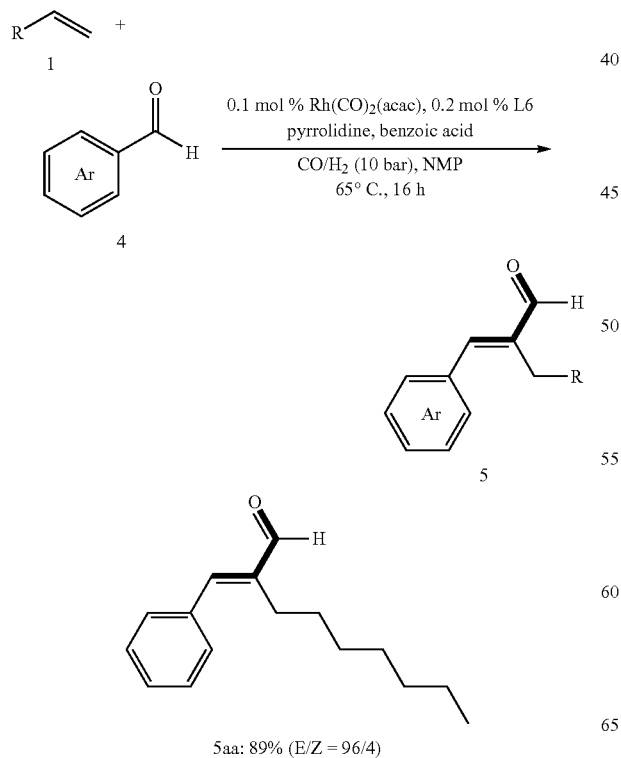

5aa: 89% (E/Z = 96/4)

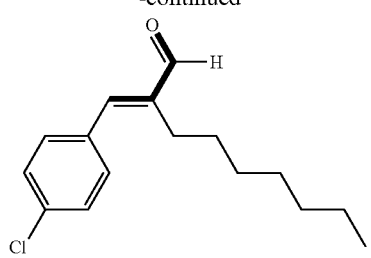

5ab: 95% (E/Z = 96/4)

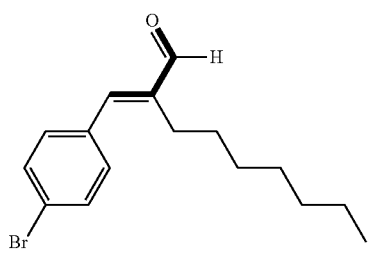

5ac: 93% (E/Z = 96/4)

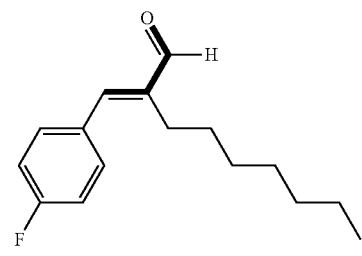

5ad: 83% (E/Z = 96/4)

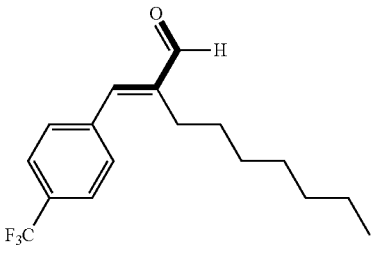

5ae: 79% (E/Z = 95/5)

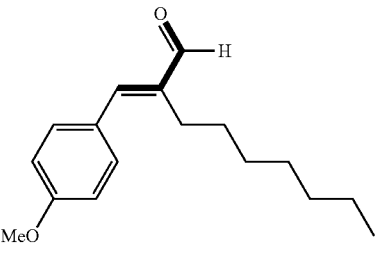

5af: 86% (E/Z = 97/3)

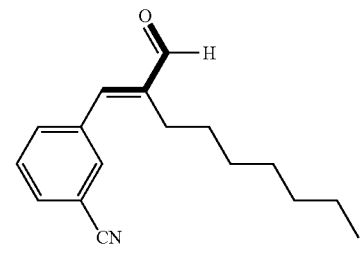

5ag: 87% (E/Z = 95/5)

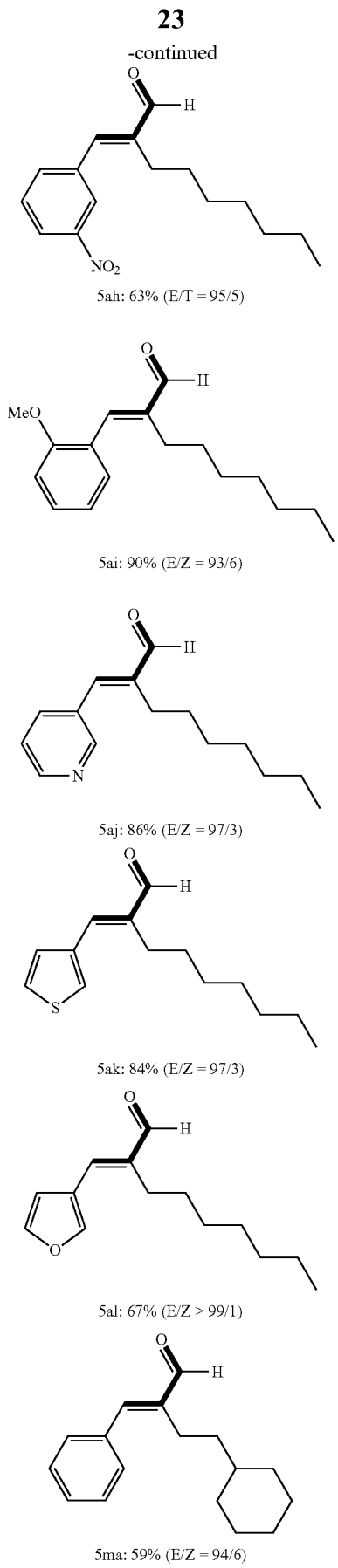

5ah: 63% (E/T = 95/5)

5ai: 90% (E/Z = 93/6)

5aj: 86% (E/Z = 97/3)

5ak: 84% (E/Z = 97/3)

5al: 67% (E/Z > 99/1)

5ma: 59% (E/Z = 94/6)

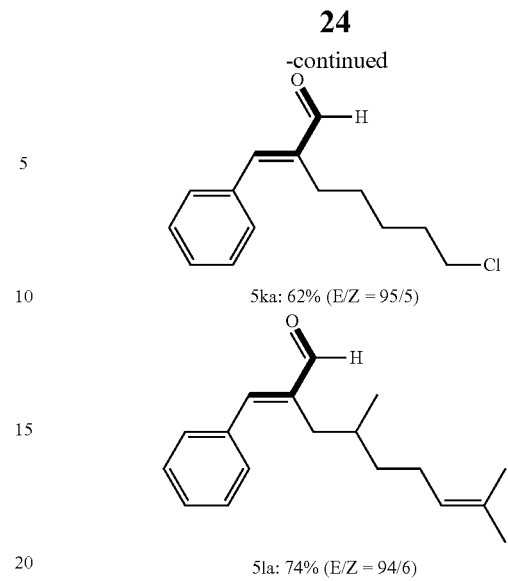

5ka: 62% (E/Z = 95/5)

5la: 74% (E/Z = 94/6)

(Scheme 1, 5aa):

A 25 mL Schlenk flask was filled with [Rh(CO)$_2$(acac)] (3.1 mg, 0.1 mol %), L6 (15.6 mg, 0.2 mol %), pyrrolidine (50 μL, 5 mol %), benzoic acid (73.2 mg, 5 mol %) and NMP (16 mL) under argon. A magnetic stirrer was placed in a 4 mL vial and 2 mL of the yellow solution from the Schlenk flask as well as 1a=1=1-octene with R=C$_6$H$_{13}$ (235 μL, 1.5 mmol) and 4a=4=benzaldehyde (153 μL, 1.5 mmol) were transferred to the vial using a syringe. The vial was placed in a stainless steel plate which was then transferred under argon into a 300 mL Series 4560 autoclave from Parr Instruments. After flushing the autoclave three times with nitrogen, it was then pressurized to 10 bar with synthesis gas (CO: H$_2$=1:1). Next, the reaction was carried out for 24 hours at 65° C. and then the autoclave was cooled to ambient temperature and the pressure was carefully released. The stereoselectivity was determined by GC/MS analysis. 2 mL of water was added to the reaction solution and extracted 3 times, each with 15 mL of ethyl acetate. The combined organic phases were washed with 45 mL of saline solution and dried over magnesium sulphate. After removal of the solvent, the residue was purified using column chromatography over silica gel (eluent:ethyl acetate:heptane=1:30) to produce the product 5aa.

Scheme 1, 5ab):

Analogous to 5aa, but p-chlorobenzaldehyde=4b (210.9 mg, 1.5 mmol) was used in place of the benzaldehyde to produce the product 5ab.

(Scheme 1, 5ac):

Analogous to 5aa, but p-bromobenzaldehyde=4c (277.5 mg, 1.5 mmol) was used in place of the benzaldehyde to produce the product 5ac.

(Scheme 1, 5ad):

Analogous to 5aa, but p-fluorobenzaldehyde=4d (186.2 mg, 1.5 mmol) was used in place of the benzaldehyde to produce the product 5ad.

(Scheme 1, 5ae):

Analogous to 5aa, but p-trifluoromethylbenzaldehyde=4e (261.2 mg, 1.5 mmol) was used in place of the benzaldehyde to produce the product 5ae.

(Scheme 1, 5af):

Analogous to 5aa, but p-methoxybenzaldehyde=4f (204.2 mg, 1.5 mmol) was used in place of the benzaldehyde to produce the product 5af.

(Scheme 1, 5aq):
Analogous to 5aa, but m-cyanobenzaldehyde=4g (196.7 mg, 1.5 mmol) was used in place of the benzaldehyde to produce the product 5ag.

(Scheme 1, 5ah):
Analogous to 5aa, but m-nitrobenzaldehyde=4h (226.7 mg, 1.5 mmol) was used in place of the benzaldehyde to produce the product 5ah.

(Scheme 1, 5ai):
Analogous to 5aa, but o-methoxybenzaldehyde=4i (204.2 mg, 1.5 mmol) was used in place of the benzaldehyde to produce the product 5ai.

(Scheme 1, 5aj):
Analogous to 5aa, but pyridine-3-carbaldehyde=4j (160.7 mg, 1.5 mmol) was used in place of the benzaldehyde to produce the product 5aj.

(Scheme 1, 5ak):
Analogous to 5aa, but thiophene-3-aldehyde=4k (168.2 mg, 1.5 mmol) was used in place of the benzaldehyde to produce the product 5ak.

(Scheme 1, 5al):
Analogous to 5aa, but furan-3-aldehyde=4l (144.1 mg, 1.5 mmol) was used in place of the benzaldehyde to produce the product 5al.

(Scheme 1, 5ma):
Analogous to 5aa, but 3-cyclohexyl-1-propene=1m (232 µL, 1.5 mmol) was used in place of 1-octene to produce product 5ma.

(Scheme 1, 5ka):
Analogous to 5aa, but 6-chloro-1-hexene=1k (198.5 µL, 1.5 mmol) was used in place of 1-octene to produce product 5ka.

(Scheme 1, 5ia):
Analogous to 5aa, but 7-methyl-3-methylocta-1,6-diene=1i (272.9 µL, 1.5 mmol) was used in place of 1-octene to produce product 5ia.

The invention claimed is:

1. A process for the production of α,β-unsaturated aldehydes from alkenes, comprising the step of:
by reacting an alkene (olefin) in the presence of a synthesis gas formed from carbon monoxide and hydrogen as well as a rhodium catalyst in combination with an organic phosphorus ligand and a co-catalyst formed from an organic amine and a weak organic acid in an organic solvent.

2. The process as claimed in claim 1, wherein a synthesis gas with a CO:H2 ratio in the range 10:1 to 1:10 is employed.

3. The process as claimed in claim 1, wherein the organic solvent is selected from the group comprising acetic acid (methyl, ethyl or n-butyl) ester and N-methyl pyrrolidone.

4. The process as claimed in claim 1, wherein the organic amine used is a primary or secondary amine, selected from the group comprising pyrrolidine, piperidine, C1-C10 alkyl (or C5-C10 cycloalkyl)- or C1-C10 dialkyl (or C5-C10-cycloalkyl)amine, morpholine and piperazine, wherein the compounds are optionally substituted.

5. The process as claimed in claim 1, wherein the weak organic acid is selected from the group comprising C6-C15 aromatic carboxylic acids, aliphatic C1-C20 carboxylic acids and heteroaromatic carboxylic acids, selected from the group comprising benzoic acid, naphthoic acid, acetic acid, pelargonic acid, thiophene carboxylic acid and nicotinic acid, wherein the compounds are optionally substituted.

6. The process as claimed in claim 1, wherein a combination of pyrrolidine and benzoic acid is used as the co-catalyst.

7. The process as claimed in claim 1, wherein the reaction temperature is 20° C. to 150° C.

8. The process as claimed in claim 1, wherein the rhodium catalyst is a rhodium complex which contains at least one of the following compounds: CO and/or olefin, halide, tetrafluoroborate, hydride, carboxylate and/or sulphate.

9. The process as claimed in claim 1, wherein the phosphorus ligands are monodentate phosphines, phosphites, phosphonites, phosphinites or bidentate phosphines, phosphonites, phosphites, phosphinites or mixed bidentate ligands being phosphine/phosphite combinations, in which the phosphorus is bound to aryl and/or (cyclo)alkyl, aryloxy and/or (cyclo)alkoxy groups.

10. The process as claimed in claim 1, wherein the rhodium:ligand ratio when using monodentate ligands is 1:50, 1:10, and when using bidentate ligands it is 1:10.

11. The process as claimed in claim 1, wherein the pressure is in the range 1 to 50 bar.

12. The process as claimed in claim 1, wherein the alkenes used are terminal alkenes, cycloalkenes and aromatic olefins containing 2 to 40 carbon atoms or mixtures, which may be substituted.

13. The process as claimed in claim 1, wherein the solvent employed is dimethylformamide or N-methyl-2-pyrrolidone.

* * * * *